United States Patent
Tockman et al.

[11] Patent Number: 6,129,750
[45] Date of Patent: Oct. 10, 2000

[54] FIXATION MECHANISM FOR A CORONARY VENOUS PACING LEAD

[75] Inventors: Bruce A. Tockman, Scandia; Randy W. Westlund, Minneapolis; Stuart R. Chastain, Shoreview; Brian D. Soltis, St. Paul; Dwight A. Skinner, Roseville, all of Minn.

[73] Assignee: Cardiac Pacemakers, Inc., St. Paul, Minn.

[21] Appl. No.: 09/274,620

[22] Filed: Mar. 23, 1999

[51] Int. Cl.[7] ............................................. A61N 1/05
[52] U.S. Cl. ............................ 607/125; 600/585; 607/122
[58] Field of Search .................................. 607/122, 126, 607/127, 125; 600/585

[56] References Cited

U.S. PATENT DOCUMENTS

| | | | |
|---|---|---|---|
| 5,405,374 | 4/1995 | Stein | 607/122 |
| 5,476,498 | 12/1995 | Ayers | 607/122 |
| 5,683,445 | 11/1997 | Swoyer | 607/125 |
| 5,722,425 | 3/1998 | Boström . | |
| 5,772,609 | 6/1998 | Nguyen et al. | 600/585 |
| 5,840,027 | 11/1998 | Swartz et al. . | |
| 5,922,014 | 7/1999 | Warman et al. | 607/122 |
| 5,924,998 | 7/1999 | Cornelius et al. | 600/585 |
| 5,925,073 | 7/1999 | Chastain et al. | 607/122 |
| 5,957,966 | 9/1999 | Schroeppel et al. | 607/122 |
| 5,997,487 | 12/1999 | Kolehmainen et al. . | |

FOREIGN PATENT DOCUMENTS

| | | | |
|---|---|---|---|
| 405049701 | 3/1993 | Japan | 607/122 |

*Primary Examiner*—Carl H. Layno
*Attorney, Agent, or Firm*—Nikolai, Mersereau & Dietz, P.A.

[57] ABSTRACT

An apparatus for fixing a cardiac lead in place within the vasculature of the heart includes a coil having a normal helical shape and a stylet for holding the coil straight during insertion of the coil through a lumen of the lead. Upon retraction of the stylet, the coil returns to its helical shape along with the lead, forcing portions of the lead into contact with the vessel wall.

28 Claims, 7 Drawing Sheets

FIXATION MECHANISM FOR A CORONARY VENOUS PACING LEAD

I. FIELD OF THE INVENTION

The present invention relates to leads for cardiac rhythm management devices such as implantable pacemakers and defibrillators. More specifically, the present invention relates to an apparatus for fixing the lead in place in the vasculature of the heart.

II. BACKGROUND OF THE INVENTION

The preferred treatment for a variety of heart conditions involves the application of electrical stimulating pulses to the heart. Appropriate courses of treatment sometimes require that such pulses be delivered to the left side of the heart and, in particular, the left ventricle. Historically, epicardial type electrodes were secured to the exterior of the heart near the apex for the purpose of delivery of such pulses. The procedure used to apply such electrodes is highly invasive and traumatic to the patient. To avoid such trauma, in recent years considerable development has occurred related to leads that can be inserted via the coronary sinus through the great vein of the heart and into the branch veins which descend from the great vein toward the apex of the heart. Current lead fixation systems on coronary vein leads are maneuverable within the vasculature but require the lead to be wedged into a narrowing vessel to achieve fixation.

Several problems exist with current fixation mechanisms, particularly when the lead and cardiac rhythm management device are being used to treat congestive heart failure. First, given the dilated nature of the heart suffering from congestive heart failure and the generally unhealthy condition of the vessels and myocardium, it is not certain that current fixation mechanisms will perform adequately. Second, current fixation designs require the electrode of the lead to be placed at or near the apex where the vessels are smaller in diameter. This location may be best with regard to fixation, but may not be the best location in terms of therapy. Emerging clinical data indicates that a mid-ventricular pacing site may be preferred in some patients suffering from congestive heart failure.

In view of the foregoing there is a real need for a fixation apparatus that will achieve lead fixation at the best location in terms of therapy even if this location is in a larger part of the vessel. More specifically, there is a need for a suitable fixation device that permits fixation of the lead at the apex, base, or mid-ventricular sites.

SUMMARY OF THE INVENTION

The present invention meets the above-described needs when used in conjunction with an over-the-wire pacing lead such as that described in U.S. Pat. No. 5,803,928 which is incorporated herein by reference or with any type of lead designed for use in the coronary veins having at least one internal lumen. The fixation mechanism is designed to be deployed in a constrained position through the lumen of the over-the-wire lead by advancing it to the desired position using a suitable deployment tool. When the fixation mechanism is properly positioned, for example in the coronary sinus, great vein, or in the branch vein, the fixation mechanism is released and assumes a biased shape within the lumen. The fixation mechanism of the present invention thus forces the lead to assume a shape similar to that of the fixation mechanism and into contact with the vessel wall and achieve fixation of the lead.

The fixation mechanism is a length of biased coil appropriately sized to fit down the central lumen of the lead when constrained by a deployment tool. Upon removal of the deployment tool, the coil is released within the lumen to impart a desired shape to the lead and place the lead in contact with the vessel wall.

A greater understanding of the present invention can be obtained from a review of the following detailed description of the preferred embodiment in view of the drawings. This description is not intended to be limiting, but rather to describe the best mode of the invention consistent with the requirements imposed by the patent statutes.

DETAILED DESCRIPTION OF THE PREFERRED EMBODIMENTS

Figure 1:
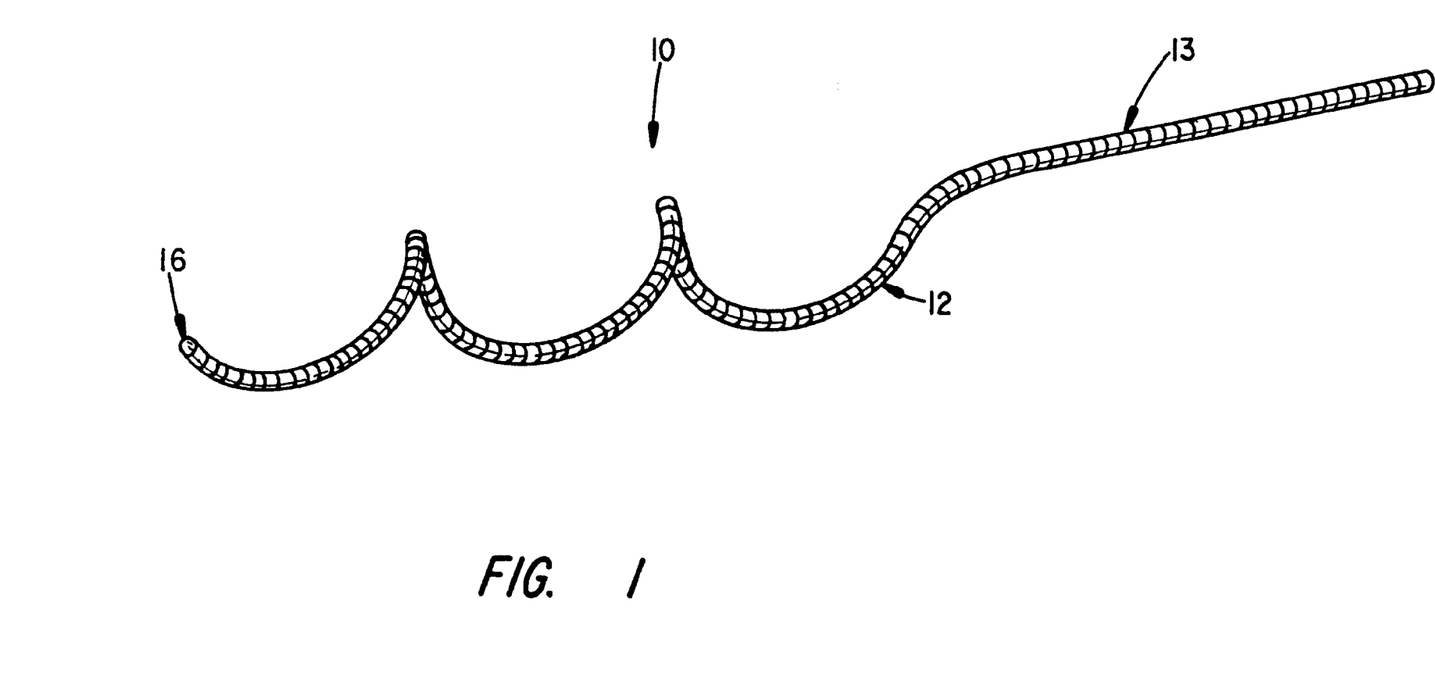
FIG. 1 is a perspective view of the fixation device of the present invention in its natural state.
Figure 3:
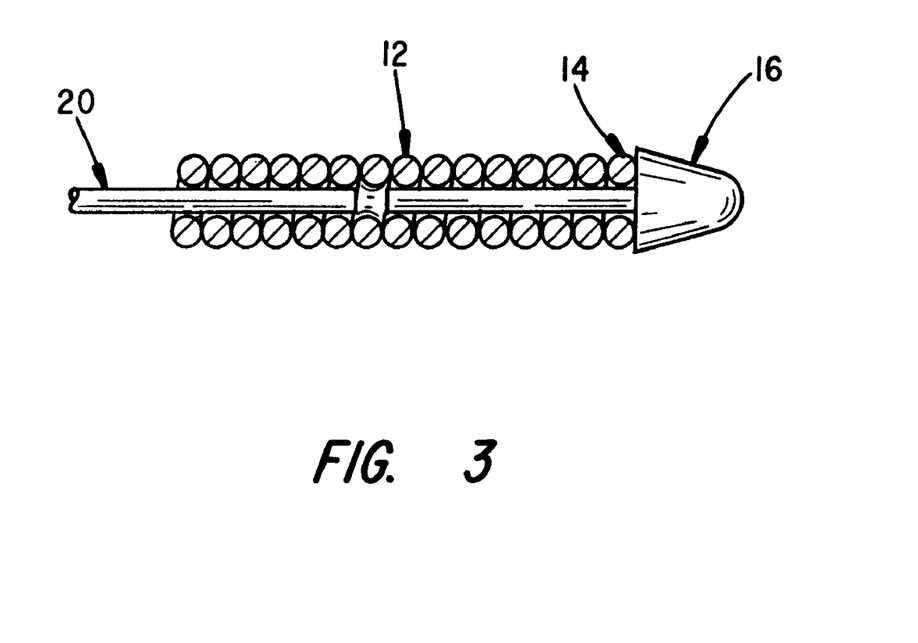
FIG. 3 is a side view showing the distal end of the fixation device.
Figure 4:
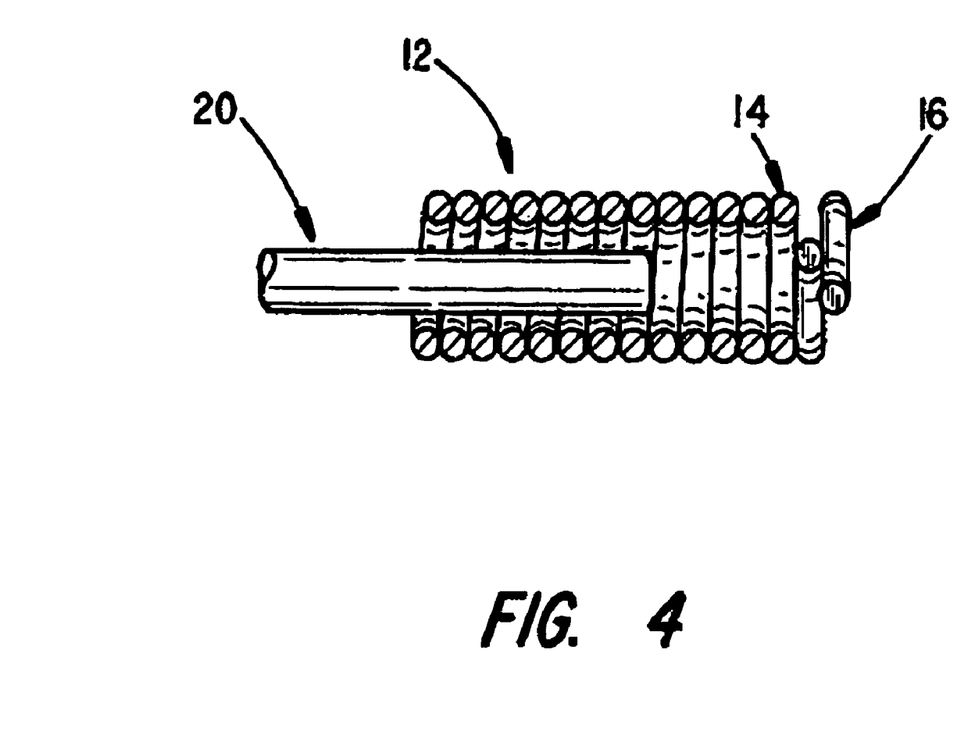
FIG. 4 is a side view of an alternative design of the distal end of the fixation device.

As shown in FIG. 1, the fixation device 10 of the present invention comprises a length of coil 13 which naturally has as a helical shape 12 at the distal end. This helical shape can be formed using a heat setting process. The overall length of the coil is preferably in the range of 20 cm to 85 cm. The length portion of the distal end having a helical shape is preferably between 2 cm and 10 cm. The helical shape could be either sinusoidal or a saw tooth wave form lying in one or more planes. The coil 13 is made from any suitable material such as nickel titanium (NiTi), MP35N, or some combination of two or more biocompatible materials and could have a unifilar, bifilar, trifilar or quadfilar construction to achieve maximum stiffness when formed into a helically biased shape. Square wire, as opposed to round wire, can be used to construct coil 13 when greater stiffness in the distal helix 12 is required in very small lumens. The length of the fixation device 10, when the distal end 12 is in its normal helical shape, is between 20 cm and 85 cm. The direction of winding for coil 13 and the helical end would preferably be opposite that of the lead. The fixation device 10 could further be coated with a hydrophilic coating or a dry film coating, such as PTFE or silicone, for maximum lubricity. The distal end 14 of the coil 13 is closed by a plug 16 made of a suitable polymer. (See FIG. 3) The plug 16 prevents the deployment stylet from projecting distally past the fixation device 10. An alternative means for retaining the deployment stylet is shown in FIG. 4. Alternatively, the distal end may be left open to aid in future extraction/removal of the fixation device.

Figure 2:
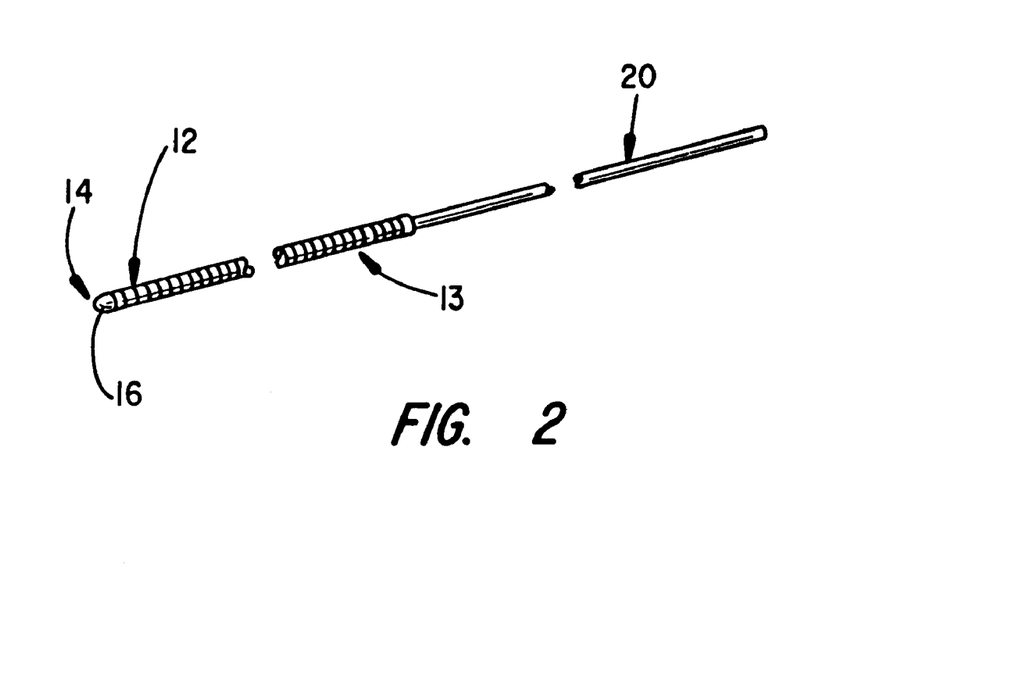
FIG. 2 is a perspective view of the fixation device of the present invention coupled to a stylet for insertion or removal of the fixation device with respect to the lead.
Figure 8:
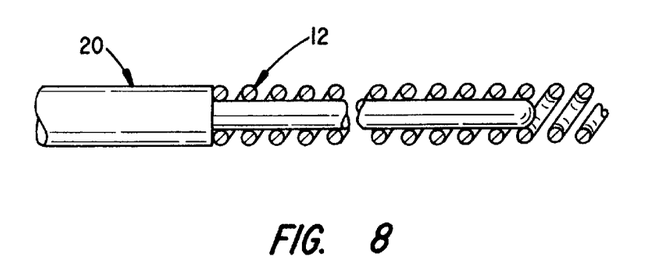
FIG. 8 is a more detailed side view showing the stylet holding the coil of the fixation device straight.

As shown in FIGS. 2 and 8, insertion of the deployment stylet 20 serves to straighten the normal helical shape 12 at the distal end of coil 13. The stylet 20 runs the length of the coil and projects proximally from the coil 13 and serves as a means for advancing the coil into position. The deployment stylet is comprised of variable stiffness materials and construction techniques to achieve maximum fixation feature deployment performance. The distal tip of the stylet, which engages the distal helix 12 requires a very stiff material such as tungsten or similar metal. The stylet may also be coated for maximum lubricity.

Figure 5:
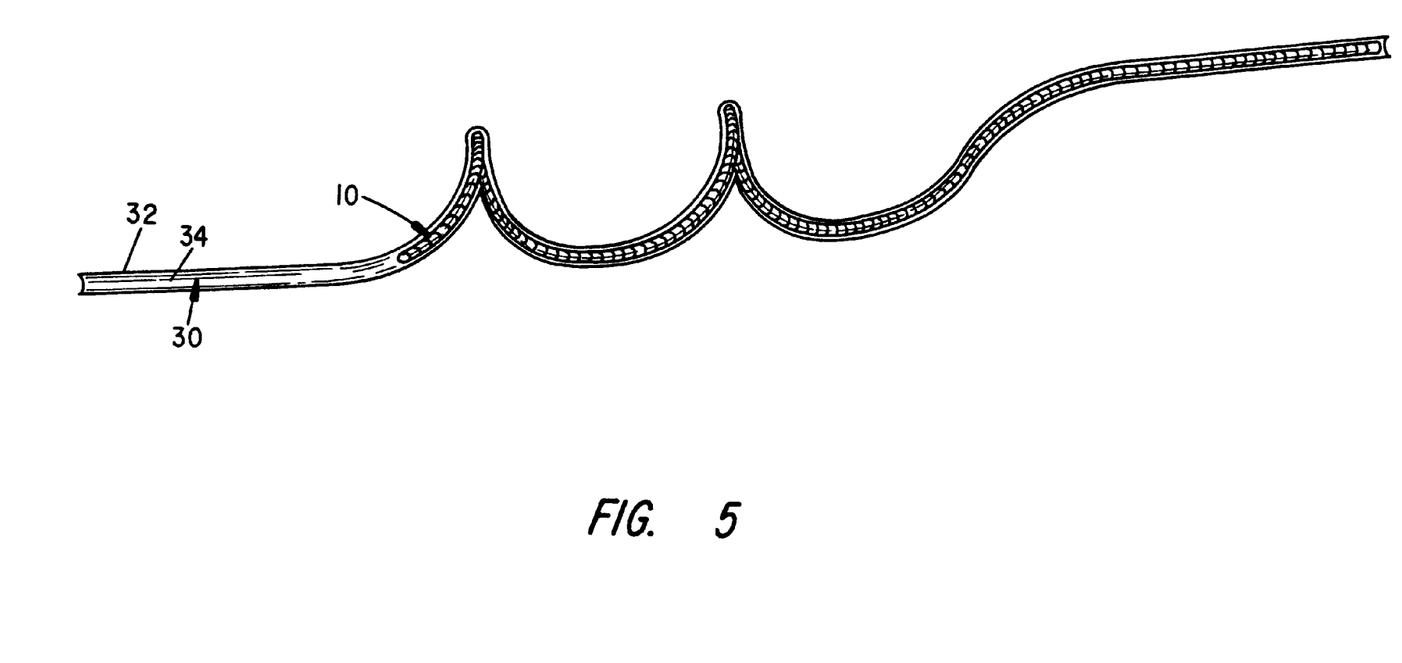
FIG. 5 is a side view showing the fixation device within a pacing lead.

FIG. 5 shows the fixation device 10 in combination with a lead 30. The lead 30 has a lead body 32 which surrounds a lumen 34 which runs the length of the lead body 32. As explained in U.S. Pat. No. 5,803,928, leads of the type shown are advanced into position using a guidewire. Once in position (see FIG. 6), the deployment stylet 20 is used to advance the fixation device 10 into position through the lumen 34. Of course, the outside diameter of the fixation device 10 when coupled to the stylet must be less than the diameter of the lumen 34. Once the fixation device 10 has been advanced through the lumen 34 to the appropriate position, the deployment stylet 20 is retracted. This causes the coil distal end 12 to resume its helical shape along with the portion of the lead body 32 surrounding the fixation device 10. As the fixation device 10 resumes its helical shape, portions of the lead body are brought into contact with the surrounding vessel wall with sufficient force to fix the lead 30 in place.

Alternatively, the fixation mechanism may be comprised of only the helical portion, known as the coil distal end 12. In this embodiment the preferred means for engaging the fixation mechanism with the deploying stylet is shown in FIG. 8.

Figure 9:
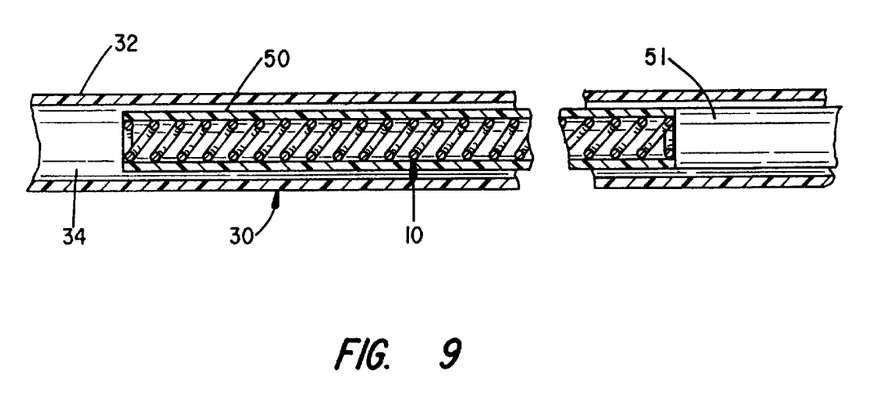
FIG. 9 is a cross-sectional of an alternative embodiment showing a coil, hypotube and ejection rod for deploying the coil within a lumen of the lead.

An alternative embodiment for the deployment tool is comprised of hypotube construction, as shown in FIG. 9. The fixation mechanism 10 is constrained within the hypotube 50 while being advanced through lumen 34 of lead 30. The fixation mechanism 10 is then pushed out of the tube 50 using an ejection rod 51 allowing the mechanism to take its natural shape. The deployment tube is comprised of stainless steel, NiTi, or other suitable metal alloys and polymeric materials for maximum flexibility in the distal regions and appropriate stiffness in the proximal regions.

Figure 6:
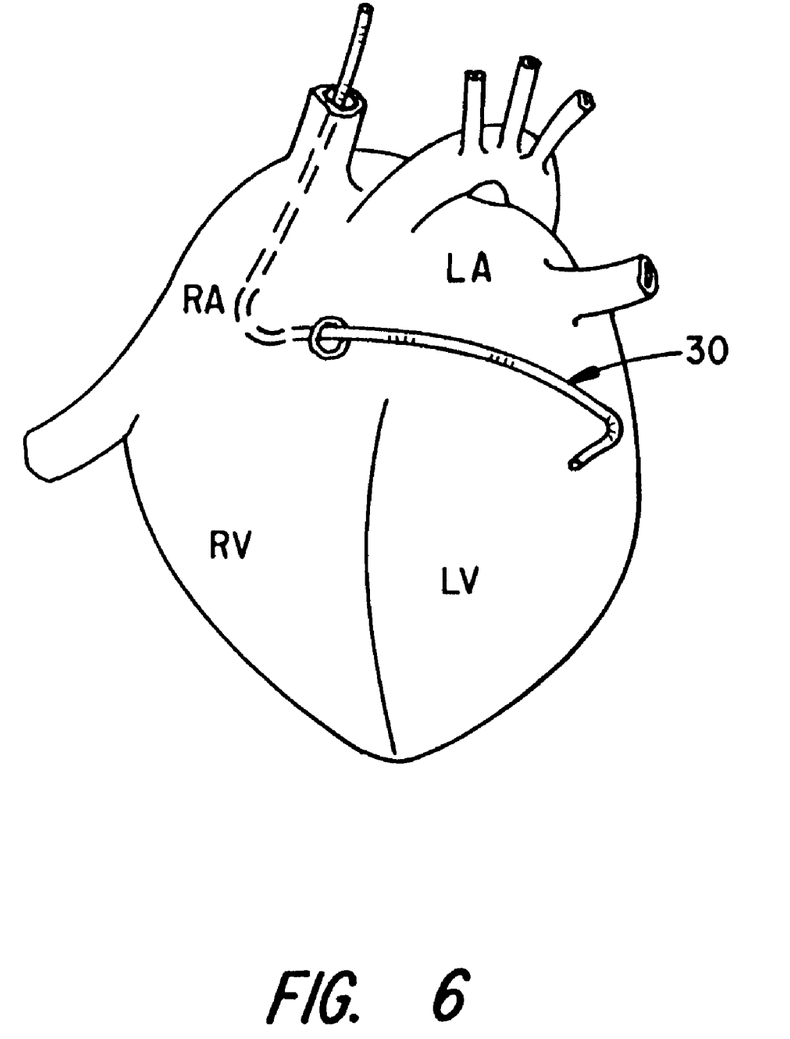
FIG. 6 is a view showing a coronary vein lead fixed in place in the heart by the fixation device.
Figure 7:
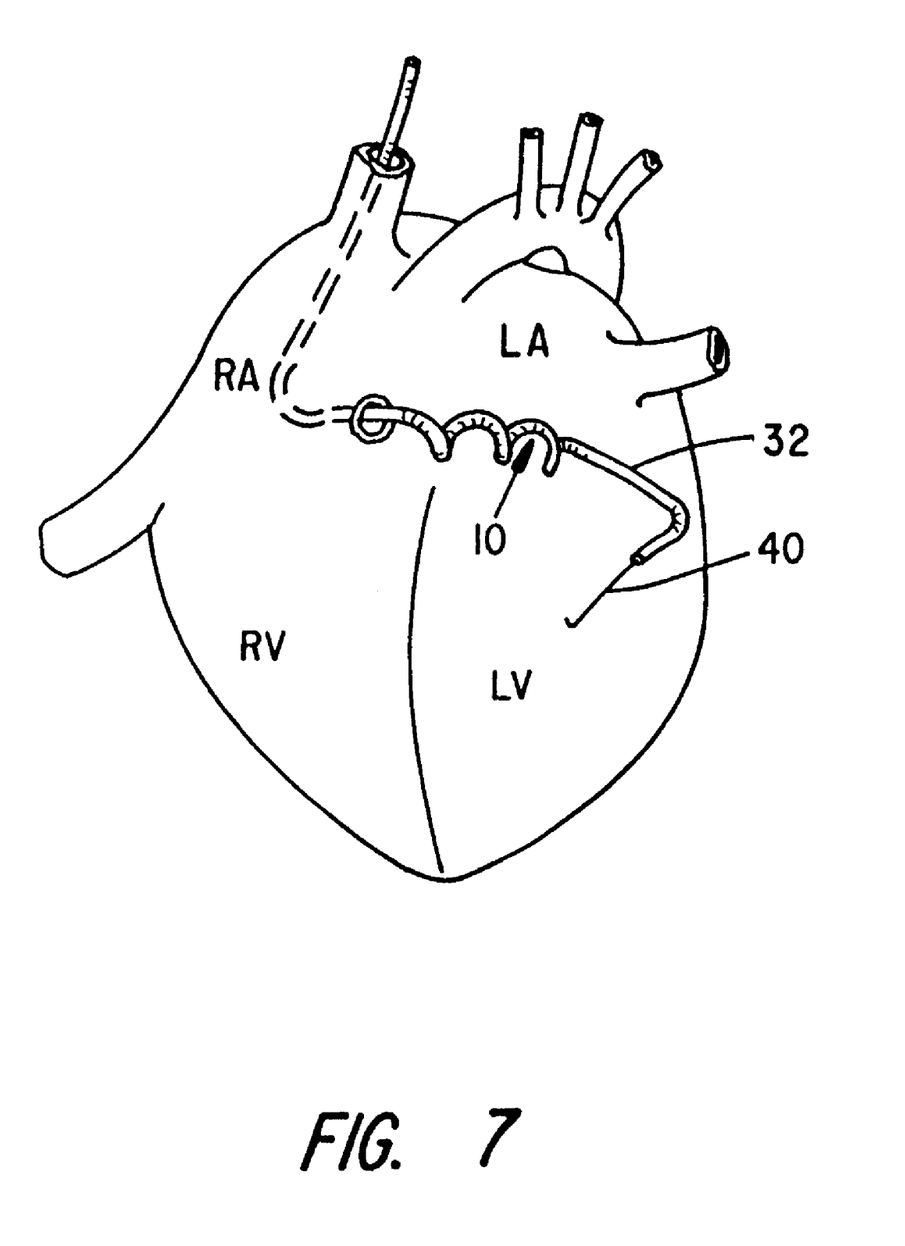
FIG. 7 is a view showing a coronary vein lead having a combined deployable inner lead structure and fixation feature, fixed in place in the heart by the fixation device.

FIGS. 6 and 7 show the manner in which the lead may be deployed. FIG. 7 shows a bipolar configuration of the lead 30. This configuration includes an inner lead body 40 which is deployable past the distal end of the lead body 32 via an orifice which extends between the distal end of the lead body 32 and the lumen 34. An integral part of this lead body 40 is the fixation device. Stylet 20 is used to straighten the inner lead body 40 while it is advanced down the lumen 34 of the outer lead body 32. After the inner lead body 40 is deployed to the desired position, stylet 20 is retracted allowing the inner lead body 40 to resume its natural shape causing the outer lead body 32 to assume a similar shape thereby fixing the bipolar lead in position.

Those skilled in the art will recognize that various materials and techniques can be used for creating a coil having a natural helical shape without departing from the present invention. For example, the coil can be wound and then heat set to provide the natural helical shape. All such techniques fall within the scope of the present invention which is defined and limited only by the following claims.

What is claimed:

1. For use in conjunction with a cardiac lead having a lumen, an apparatus for fixing said cardiac lead in place within the vasculature of the heart comprising:

(a) an internal coil having a predetermined shape and made of nickel titanium;

(b) a deployment tool for engaging and straightening the internal coil so that the coil can be inserted through a lumen of a lead into a desired position within the lead, retraction of the tool causing the internal coil to return to its predetermined shape.

2. The apparatus of claim 1 wherein said coil has a trifilar construction.

3. The apparatus of claim 1 wherein said coil has a quadfilar construction.

4. The apparatus of claim 1 wherein said coil has a unifilar construction.

5. The apparatus of claim 1 wherein said coil has a bifilar construction.

6. The apparatus of claim 1 wherein said normal predetermined shape is formed by a heat setting process.

7. The apparatus of claim 1 where the internal coil having the predetermined shape is wound in a direction different from a wound conductor in the lead in which it is deployed.

8. The apparatus of claim 1 wherein the predetermined shape is sinusoidal in that it has a two-dimensional bias, lying in one or more planes.

9. The apparatus of claim 1 wherein said coil has a plug at its distal end.

10. The apparatus of claim 9 wherein said plug is made of a polymer.

11. The apparatus of claim 10 wherein said coil has an overall length between 20 cm and 85 cm, and the distal end portion which is a wound helix has a length between 2 cm and 10 cm.

12. The apparatus of claim 1 wherein predetermined shape is a wound helix.

13. The apparatus of claim 12 wherein said distal end portion which is a wound helix has a length between 2 cm and 10 cm.

14. The apparatus of claim 1 wherein said coil is fabricated from round or square wire.

15. The apparatus of claim 1 wherein said coil is coated with a hydrophilic coating.

16. The apparatus of claim 1 wherein said coil is coated with a PTFE or silicone film coating.

17. The apparatus of claim 1 wherein said deployment tool is a stylet having variable stiffness.

18. The apparatus of claim 1 wherein said deployment tool is a coated stylet.

19. The apparatus of claim 1 wherein said deployment tool is coated with a hydrophilic coating.

20. The apparatus of claim 1 wherein said deployment tool is coated with a PTFE or silicone coating.

21. The apparatus of claim 1 wherein said deployment tool is a hypotube having variable stiffness.

22. The apparatus of claim 1 wherein said coil not only serves as a means for fixation but also a conduction means for pacing or shocking or sensing.

23. For use in conjunction with a cardiac lead having a lumen, an apparatus for fixing said cardiac lead in place within the vasculature of the heart comprising:

(a) an internal member having a predetermined shape; and (b) a stylet having variable stiffness for engaging and straightening the internal member so that the internal member can be inserted through a lumen of a lead into a desired position within the lead, retraction of the stylet causing the internal member to return to its predetrmined shape.

24. The apparatus of claim 23, wherein said stylet is coated.

25. The apparatus of claim 23, wherein said stylet is coated with a hydrophilic coating.

26. The apparatus of claim 23, wherein said stylet is coated with a PTFE or silicone coating.

27. For use in conjunction with a cardiac lead having a lumen, an apparatus for fixing said cardiac lead in place within the vasculature of the heart comprising:

(a) an internal member having a predetermined shape; and (b) a hypo tube having a variety of stiffness for engaging and straightening the internal member so that the member can be inserted through a lumen of a lead into a desired position within the lead, retraction of the hypo tube causing the internal member to return to its predetermined shape.

28. For use in conjunction with a cardiac lead having a lumen, an apparatus for fixing said cardiac lead in place within the vasculature of the heart comprising:

(a) an internal member having a predetermined shape, said internal member comprising a coil of multifilar construction; and (b) a deployment tool for engaging and straightening the internal member so that the internal member can be inserted through a lumen of a lead into a desired position within the lead, retraction of the tool causing the internal member to return to its predetermined shape.

* * * * *